United States Patent [19]
Pregnall et al.

[11] Patent Number: 4,711,854
[45] Date of Patent: Dec. 8, 1987

[54] METHOD OF MEASURING MOISTURE IN A BURNABLE ABSORBER

[75] Inventors: Richard A. Pregnall, Columbia; Archie M. LeGrand, Jr., Sumter, both of S.C.

[73] Assignee: Westinghouse Electric Corp., Pittsburgh, Pa.

[21] Appl. No.: 857,011

[22] Filed: Apr. 29, 1986

[51] Int. Cl.⁴ .......................................... G01N 33/18
[52] U.S. Cl. ................................... 436/144; 436/136; 436/157; 436/159; 422/130; 422/192; 422/308
[58] Field of Search .............. 436/136, 144, 155, 157, 436/159; 422/130, 192, 288, 308

[56] References Cited

U.S. PATENT DOCUMENTS

| | | |
|---|---|---|
| 2,932,558 | 4/1960 | Bennet . |
| 3,148,032 | 9/1964 | Bennet et al. . |
| 3,490,266 | 1/1970 | Bennet et al. . |
| 3,498,105 | 3/1970 | Hetherington . |
| 3,838,969 | 10/1974 | Dugan ................................ 436/144 |
| 3,946,228 | 3/1976 | Biermann . |
| 4,233,268 | 11/1980 | Boret et al. ........................ 422/192 |
| 4,329,868 | 5/1982 | Kuznetsov et al. ..................... 73/19 |

OTHER PUBLICATIONS

*Chemical Reaction Engineering*, O. Levenspiel, John Wiley & Sons, N.Y., New York, 1962.

Primary Examiner—S. Leon Bashore
Assistant Examiner—Lori-Ann Cody
Attorney, Agent, or Firm—R. D. Fuerle

[57] ABSTRACT

Disclosed is an apparatus for measuring the moisture content of a sample. The apparatus includes a first sealed chamber for accepting the sample and a first impulse furnace within the first chamber for dissociating water in the sample into the hydrogen and oxygen, a second sealed chamber in gaseous communication with the first chamber, a second impulse furnace within the second chamber for dissociating water and the hydrogen and the oxygen, and a hydrogen analyzer for determining the amount of hydrogen formed by the first and second impulse furnace. Also disclosed is a method of measuring the amount of water in the sample. The sample is heated in an enclosed chamber in the presence of a water dissociation catalyst, whereby water in the first chamber is dissociated into hydrogen and oxygen. Vapors are passed from the enclosed chamber to a second enclosed chamber which contains a water dissociation catalyst, whereby water in the vapors is dissociated into hydrogen and oxygen. The vapors from the second chamber are then analyzed to determine their hydrogen content.

3 Claims, 1 Drawing Figure

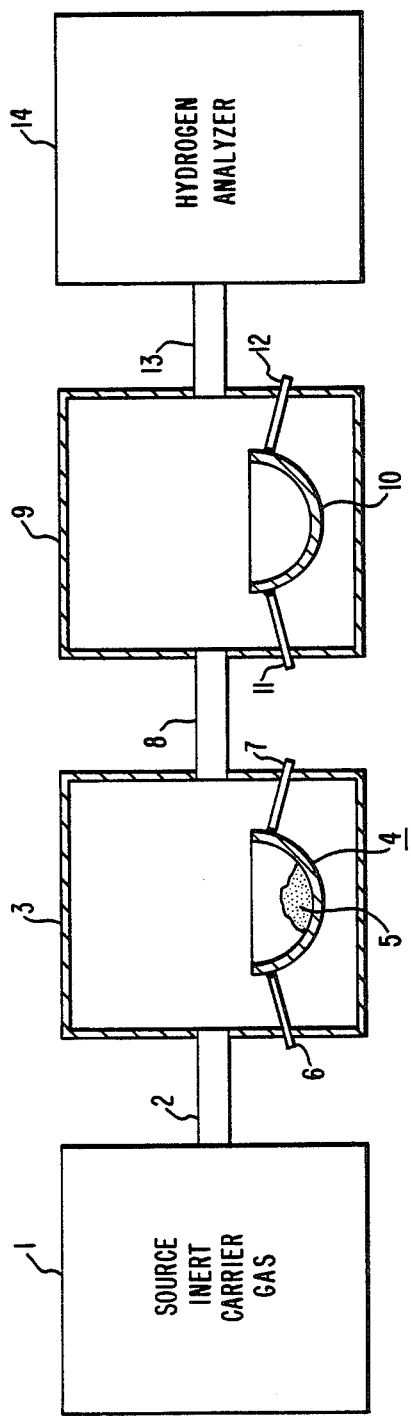

METHOD OF MEASURING MOISTURE IN A BURNABLE ABSORBER

BACKGROUND OF THE INVENTION

For many years, the nuclear industry has used a hydrogen analyzer to measure the amount of hydrogen (in the form of moisture) contained in $UO_2$ pellets. Because this measurement is very critical to the operation of a nuclear reactor, the hydrogen analyzer was studied extensively and was qualified to be accurate to meet a hydrogen specification of less than 1 ppm. To use the hydrogen analyzer, a sample was placed in a graphite crucible in an impulse furnace, rapidly heating the sample. The water given off was dissociated by the graphite crucible into hydrogen and oxygen, and the vapors were analyzed for their hydrogen content.

When improved burnable absorber materials, such as $Al_2O_3.B_4C$ annular pellets were developed, the hydrogen analyzer was also used to determine the hydrogen content in the form of moisture on these pellets. The moisture content on these pellets was required to be less than 128 ppm because the pellets were placed within zircalloy rods, and high moisture content would cause hydriding of the zircalloy and its subsequent disintegration and failure. While the hydrogen analyzer indicated that the moisture content of the pellets was less than 128 ppm, analysis of the pellets by other means indicated that the pellets had moisture contents in excess of 128 ppm.

SUMMARY OF THE INVENTION

We have discovered that the hydrogen analyzer is not accurate when the moisture content of a sample exceeds about 100 ppm and the moisture is released rapidly from the sample. We have further discovered that the hydrogen analyzer can be modified by the addition of a second furnace in series with the first furnace, and that this modification results in acceptable accuracies when the moisture content exceeds 100 ppm and the moisture is rapidly evolved, as it is with burnable absorbers.

DESCRIPTION OF THE INVENTION

The accompanying drawing is a block diagram that illustrates the apparatus and method according to this invention.

In the drawing, a source 1 of an inert carrier gas is provided that sends an inert carrier gas through line 2 into enclosed chamber 3, which contains graphite crucible 4. A sample 5 is placed within graphite crucible 4 and crucible 4 is heated through electrodes 6 and 7 by means of an implulse electric current. Vapors from enclosed chamber 3 pass through conduit 8 to enclosed chamber 9. Chamber 9 also contains a graphite crucible 10 that is heated by impulse electricity through electrodes 11 and 12. Vapors leave chamber 9 through conduit 13 and pass into hydrogen analyzer 14.

In the practice of this invention, the samples to be analyzed may be made of almost any substance, but the invention is most suitable for analyzing samples that have high moisture contents (i.e., above about 100 ppm) and which evolve the moisture rapidly on heating, such as wet annular burnable absorbers. Burn absorbers are used in nuclear reactors to even out the neutron flux in the reactor. They absorb neutrons when new fuel is present and the flux is high, then gradually burning (and absorb fewer neutrons) as the fuel becomes exhausted and the neutron flux is lower. A preferred burnable absorber is alumina that contains boron carbide, which has the formula $Al_2O_3.B_4C$.

In the first enclosed chamber, which contains the sample, means are provided to dissociate the water in the sample into hydrogen and oxygen. This is conventionally done by heating the sample in the presence of a dissociation catalyst such as graphite or platinum. The preferred dissociation catalyst is graphite because it can be formed into the shape of a crucible which can also be used to hold the sample, it is inexpensive, and a graphite crucible is conductive and therefore can be electrically heated by impulse heating.

While other means of heating the sample can also be used, electrical impulse heating is preferred because it heats the sample very rapidly so that any water in the sample is heated to its dissociation temperature while it is still in contact with the graphite.

We have found that a second enclosed chamber for dissociating water is necessary to achieve an accurate measurement of the hydrogen content of a sample. While the second enclosed chamber need not be the same as the first enclosed chamber, it is preferably identical for ease of construction and maintenance. The other portions of the apparatus, the source of inert carrier gas (e.g., argon, nitrogen, etc.), and the apparatus for analyzing hydrogen content are conventional and are well known in the art.

The following examples further illustrate this invention:

EXAMPLE 1

A conventional hydrogen analysis apparatus was used, with the exception that gases from the first enclosed chamber could be sent to a second enclosed chamber prior to analysis for hydrogen, if desired. Samples of sodium tartrate ($Na_2C_4H_4O_6$—$2H_2O$) and kaolinite ($Al_2O_3$—$2SiO_2$—$2H_2O$) were used to test the effectiveness of the apparatus with and without the second dissociation chamber. Sodium tartrate yields 3.5% hydrogen equivalent with the water molecules (15.66%) being released at 150° C. For a 0.0005 gm sample, this is equivalent to a standard of 157 micrograms of water, if all the hydrogen were present as water. Kaolinite contains 13.839% chemically combined water which is released at about 900° C. A 0.001 gm sample yields 138 micrograms of water. These two moisture standards were weighed onto pieces of aluminum foil on a five-place balance. The foil was carefully folded to contain all of the chemical. Empty foil pieces of the same size were weighed and used as blank samples prior to running the standard samples on the hydrogen analyzer. Data for the standards were adjusted for blank values obtained. The instrument was set up, calibrated, and run at 380 amps, 470 amps, and 560 amps. Both the kaolinite and sodium tartrate samples averaged a 60% increase in moisture dissociated and measured at 380 amps when both heating chambers were used, over using just a single heating chamber. At 470 amps the kaolinite standard averaged a 25% increase in measurement accuracy and the sodium tartrate standards averaged about 50% improvement. At 560 amps, the kaolinite did not show an improvement, but the sodium tartrate improved from 66.5% to 87.3% when the double heating was used.

EXAMPLE 2

Example 1 was repeated using samples of a wet annular burnable absorber which consisted of $Al_2O_3 \cdot B_4C$. The samples, which were cut from the same pellet, increased in average ppm moisture measured from 51 to 201 at 380 amps as received, and from 33 to 100 ppm after drying at 500° C.S for one hour when the double furnace was used.

What is claimed is:

1. A method of measuring the amount of moisture contained in a sample of a burnable absorber having a moisture content in excess of 100 ppm comprising:
   (1) heating said sample in a first enclosed chamber in the presence of a water dissociation catalyst, whereby water in said sample is dissociated into hydrogen and oxygen;
   (2) passing vapors from said first enclosed chamber to a second enclosed chamber which contains a water dissociation catalyst, whereby water in said vapors is dissociated into hydrogen and oxygen;
   (3) analyzing said vapors from said second enclosed chamber to determine their hydrogen content.

2. A method according to claim 1 wherein said burnable absorber is $Al_2O_3 \cdot B_4C$.

3. A method according to claim 1 wherein said sample is placed in a graphite crucible in said first chamber, and said crucible is heated by electrical impulse.

* * * * *